United States Patent
Lubitz et al.

(10) Patent No.: US 6,964,845 B1
(45) Date of Patent: Nov. 15, 2005

(54) THERMOSTABLE PHAGE LAMBDA OPERATOR MUTANTS FOR REGULATING GENE EXPRESSION

(76) Inventors: Werner Lubitz, Schönborngasse 12/7, A-1080 Vienna (AT); Wolfgang Jechlinger, Strozzigasse 38/12, A-1080 Vienna (AT); Michael Szostak, In den Schnablern 9/3, A-2344 Maria Enzersdorf (AT); Angela Witte, Gabelsbergergasse 6/8, A-1020 Vienna (AT)

(*) Notice: Subject to any disclaimer, the term of this patent is extended or adjusted under 35 U.S.C. 154(b) by 0 days.

(21) Appl. No.: 09/147,693
(22) PCT Filed: Aug. 21, 1997
(86) PCT No.: PCT/EP97/04560
  § 371 (c)(1),
  (2), (4) Date: Feb. 17, 1999
(87) PCT Pub. No.: WO98/07874
  PCT Pub. Date: Feb. 26, 1998

(30) Foreign Application Priority Data
Aug. 21, 1996 (DE) .......................... 196 33 698

(51) Int. Cl.⁷ ................. C12N 15/00; C12N 15/09; C12N 1/20; C12Q 1/68; C07H 21/04
(52) U.S. Cl. .............. 435/6; 435/69.1; 435/320.1; 435/471; 435/488; 435/235.1; 435/252.3; 536/24.1; 536/23.1
(58) Field of Search .............. 536/24.1, 23.1; 435/6, 69.1, 471, 488, 320.1, 235.1, 252.3; 514/2, 44

(56) References Cited
U.S. PATENT DOCUMENTS
4,634,678 A * 1/1987 Salstrom et al. ............ 435/317
5,576,190 A * 11/1996 Belagaje et al. ............ 435/69.1
5,811,093 A * 9/1998 Merril et al. ............... 424/93.6

FOREIGN PATENT DOCUMENTS
| WO | WO 91/13155 | 9/1991 |
| WO | 91/13155 | 9/1991 |
| WO | WO 95/34643 | 12/1995 |
| WO | WO96/06164 | * 2/1996 |

OTHER PUBLICATIONS

Panthel et al. Generation of *Helicobacter pylori* ghosts by PhiX protein E–mediated inactivation and their evaluation as vaccine candidates. Infection and Immunity vol. 71(1):109–116, 2003.*

Miller Curr. Opinion in Infect. Dis., vol. 10:183–189, 1997.*

Gregoriadis Pharm. Res. vol. 15(5):661–670, 1998, (Abstract).*

Chen et al. Mutation in the bacteriophage lambda pL/oL region that spontaneously occur in plasmid pRPZ126. Mutation Res. vol. 228:81–87, Jan. 1990.*

Szostak et al. Vaccines 93. Cold Spring Harbor Laboratory Press. 419–425, Dec. 1993.*

Benson et al. DNA sequence determinants of lambda repressor binding in vivo. Genetics vol. 188:21–29, Jan. 1988.*

(Continued)

*Primary Examiner*—Gerry Leffers
(74) *Attorney, Agent, or Firm*—Rothwell, Figg, Ernst & Manbeck

(57) ABSTRACT

The present invention concerns a method for selecting New $P_R$ or $P_L$ operator sequences from lambdoid phages which have different thermostability compared to the wild-type sequence with regard to binding a repressor. In addition new mutated $P_R$ or $P_L$ operator sequences and their use for the temperature-regulated expression of genes and for production of improved vaccines is disclosed.

26 Claims, 5 Drawing Sheets

OTHER PUBLICATIONS

Zacharias et al. Combined conformational search and finite-difference Poisson–Boltzmann approach to flexible docking. J. Mol. Biol. vol. 238:455–465, Mar. 1994.*

Ellis, RW New technologies for making vaccines. in VACCINES, W B Saunders Company, Plotkin and Mortimer, eds. pp. 568–575, Jan. 1988.*

Vasquez et al. Controlled expression of click beetle luciferase using a bacterial operator–repressor system. FEMS Microbiol. Letters. vol. 121:11–18, Jul. 1994.*

Pakula et al. Amino acid substitutions that increase the thermal stability of the lambda Cro protein. Proteins: Structure, Function, and Genetics. vol. 5:202–210, Jun. 1989.*

Eliason et al. NH–terminal arm of phage lambda repressor contributes energy and specificity to repressor binding and determines the effects of operator mutations. PNAS vol. 82–2339–2343, Apr. 1985.*

Hayes. S. and Hayes, C., "Spontaneous λ $o_R$ Mutations Suppress Inhibition of Bacteriophage Growth by Nonimmune Exclusion Phenotype of Defective λ Prophage," *Journal of Virology* 58(3):835–842, Jun. 1986.

Bailone, A. and Galabert, F., "Nucleotide sequence of the operators of λ ultravirulent mutants," *Nucl. Acids Res.* 8(10):2147–2164, 1980.

Remaut, E., et al., Plasmid vectors for high–efficiency expression controlled by the $p_L$ promoter of coliphage lambda, *Gene* 15:81–93, 1981.

Hensel, A. et al., "Oral Immunization of Pigs with Viable or Inactivated *Actinobacillus pleuropneumoniae* Serotype 9 Induces Pulmonary and Systemic Antibodies and Protects against Homologous Aerosol Challenge," *Infection and Immunity* 63(8):3048–3053, Aug. 1995.

Voet, D. and Voet, J.G., "Der Repressor stimuliert sein eigene Synthese, während er alle anderen λ–Gene abshaltet," *Biochemistry* 1024–1026, 1992, No Translation Provided.

Hershberger et al., The Journal of Biological Chemistry, vol. 268, No. 12, Issue of Apr. 25, pp 8943–8948, "Interference by $P_R$–bound RNA Polymerase with $P_{RM}$ Function in Vitro".

* cited by examiner

SEQUENCE LISTING

<160> NUMBER OF SEQ ID NOS: 11

<210> SEQ ID NO 1
<211> LENGTH: 82
<212> TYPE: DNA
<213> ORGANISM: Lambda-OR-Operator (wild type)

<400> SEQUENCE: 1
acgttaaatc tatcaccgca agggataaat atctaacacc gtgcgtgttg actattttac    60
ctctggcggt gataatggtt gc                                             82

<210> SEQ ID NO 2
<211> LENGTH: 82
<212> TYPE: DNA
<213> ORGANISM: Lambda-OR-Operator (mutant)

<400> SEQUENCE: 2
acgttaaatc tatcaccgca agggataaat atctaacacc gcgcgtgttg actattttac    60
ctctggcggt gataatggtt gc                                             82

<210> SEQ ID NO 3
<211> LENGTH: 85
<212> TYPE: DNA
<213> ORGANISM: Lambda-OL-Operator (wild type)

<400> SEQUENCE: 3
acatacagat aaccatctgc ggtgataaat tatctctggc ggtgttgaca taaataccac    60
tggcggtgat actgagcaca tcagc                                          85

<210> SEQ ID NO 4
<211> LENGTH: 1601
<212> TYPE: DNA
<213> ORGANISM: pAW12 Fragment
<220> FEATURE:
<221> NAME/KEY: CDS
<222> LOCATION: Complement ((106)..(816))
<220> FEATURE:
<221> NAME/KEY: CDS
<222> LOCATION: (1144)..(1416)

<400> SEQUENCE: 4
atttactatg ttatgttctg aggggagtga aaattcccct aattcgatga agattcttgc    60
tcaattgtta tcagctatgc gccgaccaga acaccttgcc gatcagccaa acgtctcttc   120
aggccactga ctagcgataa cttccccac aacggaacaa ctctcattgc atgggatcat    180
tgggtactgt gggtttagtg gttgtaaaaa cacctgaccg ctatccctga tcagtttctt   240
gaaggtaaac tcatcacccc caagtctggc tatgcagaaa tcacctggct caacagcctg   300
ctcagggtca acgagaatta acattccgtc aggaaagctt ggcttggagc tgttggtgc    360 ggtcatggaa ttaccttcaa cctcaagcca gaatgcagaa tcactggctt ttttggttgt   420
gcttacccat ctctccgcat caccttggt aaaggttcta agcttaggtg agaacatccc    480
tgcctgaaca tgagaaaaaa cagggtactc atactcactt ctaagtgacg gctgcatact   540
aaccgcttca tacatctcgt agatttctct ggcgattgaa gggctaaatt cttcaacgct   600
aactttgaga attttgtaa gcaatgcggc gttataagca tttaatgcat tgatgccatt   660
aaataaagca ccaacgcctg actgccccat cccatcttg tctgcgacag attcctggga   720
taagccaagt tcattttct ttttttcata aattgcttta aggcgacgtg cgtcctcaag   780

-continued

```
ctgctcttgt gttaatggtt tcttttttgt gctcatacgt taaatctatc accgcaaggg       840
ataaatatct aacaccgcgc gtgttgacta ttttacctct ggcggtgata atggttgcat       900
gtactaagta ggttgtatgg aacaacgcat aaccctgaaa gattatgcaa tgcgctttgg       960
gcaaaccaag acagctaaag atcctctaga gtcgacctgc aggcatgcaa gcttatcgaa      1020
ttctcattca ggcttctgcc gttttggatt taaccgaaga tgatttcgat tttctgacga      1080
gtaacaaagt ttggattgct actgaccgct ctcgtgctcg tcgctgcgtt gaggcttgcg      1140 ttt atg gta cgc tgg act ttg tgg gat acc ctc gct ttc ctg ctc ctg       1188
    Met Val Arg Trp Thr Leu Trp Asp Thr Leu Ala Phe Leu Leu Leu
    1               5                   10                  15 ttg agt tta ttg ctg ccg tca ttg ctt att atg ttc atc ccg tca aca       1236
Leu Ser Leu Leu Leu Pro Ser Leu Leu Ile Met Phe Ile Pro Ser Thr
                20                  25                  30 ttc aaa cgg cct gtc tca tca tgg aag gcg ctg aat tta cgg aaa aca       1284
Phe Lys Arg Pro Val Ser Ser Trp Lys Ala Leu Asn Leu Arg Lys Thr
            35                  40                  45 tta tta atg gcg tcg agc gtc cgg tta aag ccg ctg aat tgt tcg cgt       1332
Leu Leu Met Ala Ser Ser Val Arg Leu Lys Pro Leu Asn Cys Ser Arg
        50                  55                  60 tta cct tgc gtg tac gcg cag gaa aca ctg acg ttc tta ctg acg cag       1380
Leu Pro Cys Val Tyr Ala Gln Glu Thr Leu Thr Phe Leu Leu Thr Gln
    65                  70                  75 aag aaa acg tgc gtc aaa aat tac gtg cag aag gag tgatgtaatg            1426
Lys Lys Thr Cys Val Lys Asn Tyr Val Gln Lys Glu
80                  85                  90 tctaaaggta aaaacgttc tggcgctcgc cctggtcgtc cgcagccgtt gcgaggtact      1486
aaaggcaagc gtaaaggcgc tcgtctttgg tatgtaggtg gtcaacaatt ttaattgcag     1546
gggcttcggc ccttacttga ggataaaatta tgtctaatat tcaaactggc gccga         1601
```

<210> SEQ ID NO 5
<211> LENGTH: 237
<212> TYPE: PRT
<213> ORGANISM: pAW12 Fragment

<400> SEQUENCE: 5

```
Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Thr Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160
```

```
Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
                195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 6
<211> LENGTH: 91
<212> TYPE: PRT
<213> ORGANISM: pAW12 Fragment

<400> SEQUENCE: 6

Met Val Arg Trp Thr Leu Trp Asp Thr Leu Ala Phe Leu Leu Leu Leu
 1               5                  10                  15

Ser Leu Leu Pro Ser Leu Leu Ile Met Phe Ile Pro Ser Thr Phe
                20                  25                  30

Lys Arg Pro Val Ser Ser Trp Lys Ala Leu Asn Leu Arg Lys Thr Leu
            35                  40                  45

Leu Met Ala Ser Ser Val Arg Leu Lys Pro Leu Asn Cys Ser Arg Leu
    50                  55                  60

Pro Cys Val Tyr Ala Gln Glu Thr Leu Thr Phe Leu Leu Thr Gln Lys
65                  70                  75                  80

Lys Thr Cys Val Lys Asn Tyr Val Gln Lys Glu
                85                  90

<210> SEQ ID NO 7
<211> LENGTH: 2834
<212> TYPE: DNA
<213> ORGANISM: pCSJ Fragment
<220> FEATURE:
<221> NAME/KEY: CDS
<222> LOCATION: Complement ((106)..(816)
<220> FEATURE:
<221> NAME/KEY: CDS
<222> LOCATION: (1025)..(2104)
<220> FEATURE:
<221> NAME/KEY: CDS
<222> LOCATION: (2377)..(2649)

<400> SEQUENCE: 7
atttactatg ttatgttctg aggggagtga aaattcccct aattcgatga agattcttgc      60
tcaattgtta tcagctatgc gccgaccaga acaccttgcc gatcagccaa acgtctcttc    120
aggccactga ctagcgataa ctttccccac aacggaacaa ctctcattgc atgggatcat    180
tgggtactgt gggtttagtg gttgtaaaaa cacctgaccg ctatccctga tcagtttctt    240
gaaggtaaac tcatcacccc caagtctggc tatgcagaaa tcacctggct caacagcctg    300
ctcagggtca acgagaatta acattccgtc aggaaagctt ggcttggagc tgttggtgc    360 ggtcatggaa ttaccttcaa cctcaagcca gaatgcagaa tcactggctt ttttggttgt    420
gcttacccat ctctccgcat caccttttggt aaaggttcta agcttaggtg agaacatccc    480
tgcctgaaca tgagaaaaaa cagggtactc atactcactt ctaagtgacg gctgcatact    540
aaccgcttca tacatctcgt agatttctct ggcgattgaa gggctaaatt cttcaacgct    600
aactttgaga atttttgtaa gcaatgcggc gttataagca tttaatgcat tgatgccatt    660
```

-continued

```
aaataaagca ccaacgcctg actgccccat ccccatcttg tctgcgacag attcctggga       720
taagccaagt tcattttcct ttttttcata aattgcttta aggcgacgtg cgtcctcaag       780
ctgctcttgt gttaatggtt tcttttttgt gctcatacgt taaatctatc accgcaaggg       840
ataaatatct aacaccgcgc gtgttgacta ttttacctct ggcggtgata atggttgcat       900
gtactaagta ggttgtatgg aacaacgcat aaccctgaaa gattatgcaa tgcgctttgg       960
gcaaaccaag acagctaaag atcctctaga gcgcccggaa gagagtcaat tcagggtggt      1020 gaat gtg aaa cca gta acg tta tac gat gtc gca gag tat gcc ggt gtc      1069
     Val Lys Pro Val Thr Leu Tyr Asp Val Ala Glu Tyr Ala Gly Val
      1               5                  10                  15 tct tat cag acc gtt tcc cgc gtg gtg aac cag gcc agc cac gtt tct      1117
Ser Tyr Gln Thr Val Ser Arg Val Val Asn Gln Ala Ser His Val Ser
                 20                  25                  30 gcg aaa acg cgg gaa aaa gtg gaa gcg gcg atg gcg gag ctg aat tac      1165
Ala Lys Thr Arg Glu Lys Val Glu Ala Ala Met Ala Glu Leu Asn Tyr
             35                  40                  45 att ccc aac cgc gtg gca caa caa ctg gcg ggc aaa cag tcg ttg ctg      1213
Ile Pro Asn Arg Val Ala Gln Gln Leu Ala Gly Lys Gln Ser Leu Leu
         50                  55                  60 att ggc gtt gcc acc tcc agt ctg gcc ctg cac gcg ccg tcg caa att      1261
Ile Gly Val Ala Thr Ser Ser Leu Ala Leu His Ala Pro Ser Gln Ile
     65                  70                  75 gtc gcg gcg att aaa tct cgc gcc gat caa ctg ggt gcc agc gtg gtg      1309
Val Ala Ala Ile Lys Ser Arg Ala Asp Gln Leu Gly Ala Ser Val Val
 80                  85                  90                  95 gtg tcg atg gta gaa cga agc ggc gtc gaa gcc tgt aaa gcg gcg gtg      1357
Val Ser Met Val Glu Arg Ser Gly Val Glu Ala Cys Lys Ala Ala Val
                 100                 105                 110 cac aat ctt ctc gcg caa cgc gtc agt ggg ctg atc att aac tat ccg      1405
His Asn Leu Leu Ala Gln Arg Val Ser Gly Leu Ile Ile Asn Tyr Pro
             115                 120                 125 ctg gat gac cag gat gcc att gct gtg gaa gct gcc tgc act aat gtt      1453
Leu Asp Asp Gln Asp Ala Ile Ala Val Glu Ala Ala Cys Thr Asn Val
         130                 135                 140 ccg gcg tta ttt ctt gat gtc tct gac cag aca ccc atc aac agt att      1501
Pro Ala Leu Phe Leu Asp Val Ser Asp Gln Thr Pro Ile Asn Ser Ile
     145                 150                 155 att ttc tcc cat gaa gac ggt acg cga ctg ggc gtg gag cat ctg gtc      1549
Ile Phe Ser His Glu Asp Gly Thr Arg Leu Gly Val Glu His Leu Val
 160                 165                 170                 175 gca ttg ggt cac cag caa atc gcg ctg tta gcg ggc cca tta agt tct      1597
Ala Leu Gly His Gln Gln Ile Ala Leu Leu Ala Gly Pro Leu Ser Ser
                 180                 185                 190 gtc tcg gcg cgt ctg cgt ctg gct ggc tgg cat aaa tat ctc act cgc      1645
Val Ser Ala Arg Leu Arg Leu Ala Gly Trp His Lys Tyr Leu Thr Arg
             195                 200                 205 aat caa att cag ccg ata gcg gaa cgg gaa ggc gac tgg agt gcc atg      1693
Asn Gln Ile Gln Pro Ile Ala Glu Arg Glu Gly Asp Trp Ser Ala Met
         210                 215                 220 tcc ggt ttt caa caa acc atg caa atg ctg aat gag ggc atc gtt ccc      1741
Ser Gly Phe Gln Gln Thr Met Gln Met Leu Asn Glu Gly Ile Val Pro
     225                 230                 235 act gcg atg ctg gtt gcc aac gat cag atg gcg ctg ggc gca atg cgc      1789
Thr Ala Met Leu Val Ala Asn Asp Gln Met Ala Leu Gly Ala Met Arg
 240                 245                 250                 255 gcc att acc gag tcc ggg ctg cgc gtt ggt gcg gat atc tcg gta gtg      1837
Ala Ile Thr Glu Ser Gly Leu Arg Val Gly Ala Asp Ile Ser Val Val
                 260                 265                 270
```

```
gga tac gac gat acc gaa gac agc tca tgt tat atc ccg ccg tca acc      1885
Gly Tyr Asp Asp Thr Glu Asp Ser Ser Cys Tyr Ile Pro Pro Ser Thr
            275                 280                 285 acc atc aaa cag gat ttt cgc ctg ctg ggg caa acc agc gtg gac cgc      1933
Thr Ile Lys Gln Asp Phe Arg Leu Leu Gly Gln Thr Ser Val Asp Arg
        290                 295                 300 ttg ctg caa ctc tct cag ggc cag gcg gtg aag ggc aat cag ctg ttg      1981
Leu Leu Gln Leu Ser Gln Gly Gln Ala Val Lys Gly Asn Gln Leu Leu
305                 310                 315 ccc gtc tca ctg gtg aaa aga aaa acc acc ctg gcg ccc aat acg caa      2029
Pro Val Ser Leu Val Lys Arg Lys Thr Thr Leu Ala Pro Asn Thr Gln
320                 325                 330                 335 acc gcc tct ccc cgc gcg ttg gcc gat tca tta atg cag ctg gca cga      2077
Thr Ala Ser Pro Arg Ala Leu Ala Asp Ser Leu Met Gln Leu Ala Arg
                340                 345                 350 cag gtt tcc cga ctg gaa agc ggg cag tgagcgcaac gcaattaatg            2124
Gln Val Ser Arg Leu Glu Ser Gly Gln
            355                 360 tgagttagct cactcattag cacccagg ctttacactt tatgcttccg gctcgtatgt      2184
tgtgtggaat tgtgagcgga taacaatttc acacaggaaa cagctctgca ggcatgcaag    2244
cttatcgaat tctcattcag gcttctgccg ttttggattt aaccgaagat gatttcgatt    2304
ttctgacgag taacaaagtt tggattgcta ctgaccgctc tcgtgctcgt cgctgcgttg    2364
aggcttgcgt tt atg gta cgc tgg act ttg tgg gat acc ctc gct ttc ctg    2415
            Met Val Arg Trp Thr Leu Trp Asp Thr Leu Ala Phe Leu
                                365                 370 ctc ctg ttg agt tta ttg ctg ccg tca ttg ctt att atg ttc atc ccg      2463
Leu Leu Leu Ser Leu Leu Leu Pro Ser Leu Leu Ile Met Phe Ile Pro
375                 380                 385 tca aca ttc aaa cgg cct gtc tca tca tgg aag gcg ctg aat tta cgg      2511
Ser Thr Phe Lys Arg Pro Val Ser Ser Trp Lys Ala Leu Asn Leu Arg
390                 395                 400                 405 aaa aca tta tta atg gcg tcg agc gtc cgg tta aag ccg ctg aat tgt      2559
Lys Thr Leu Leu Met Ala Ser Ser Val Arg Leu Lys Pro Leu Asn Cys
            410                 415                 420 tcg cgt tta cct tgc gtg tac gcg cag gaa aca ctg acg ttc tta ctg      2607
Ser Arg Leu Pro Cys Val Tyr Ala Gln Glu Thr Leu Thr Phe Leu Leu
                425                 430                 435 acg cag aag aaa acg tgc gtc aaa aat tac gtg cag aag gag                2649
Thr Gln Lys Lys Thr Cys Val Lys Asn Tyr Val Gln Lys Glu
            440                 445                 450 tgatgtaatg tctaaaggta aaaaacgttc tggcgctcgc cctggtcgtc cgcagccgtt    2709
gcgaggtact aaaggcaagc gtaaaggcgc tcgtctttgg tatgtaggtg gtcaacaatt    2769
ttaattgcag gggcttcggc ccttacttga ggataaatta tgtctaatat tcaaactggc    2829
gccga                                                                2834

<210> SEQ ID NO 8
<211> LENGTH: 237
<212> TYPE: PRT
<213> ORGANISM: pCSJ Fragment

<400> SEQUENCE: 8

Met Ser Thr Lys Lys Pro Leu Thr Gln Glu Gln Leu Glu Asp Ala
 1               5                  10                  15

Arg Arg Leu Lys Ala Ile Tyr Glu Lys Lys Lys Asn Glu Leu Gly Leu
            20                  25                  30
```

```
Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
        50                  55                  60

Leu Leu Thr Lys Ile Leu Lys Val Ser Val Glu Phe Ser Pro Ser
65                  70                  75                  80

Ile Ala Arg Glu Ile Tyr Glu Met Tyr Glu Ala Val Ser Met Gln Pro
                    85                  90                  95

Ser Leu Arg Ser Glu Tyr Glu Tyr Pro Val Phe Ser His Val Gln Ala
                    100                 105                 110

Gly Met Phe Ser Pro Lys Leu Arg Thr Phe Thr Lys Gly Asp Ala Glu
            115                 120                 125

Arg Trp Val Ser Thr Lys Lys Ala Ser Asp Ser Ala Phe Trp Leu
        130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Gln Ala Val Glu
                    165                 170                 175

Pro Gly Asp Phe Cys Ile Ala Arg Leu Gly Gly Asp Glu Phe Thr Phe
                    180                 185                 190

Lys Lys Leu Ile Arg Asp Ser Gly Gln Val Phe Leu Gln Pro Leu Asn
            195                 200                 205

Pro Gln Tyr Pro Met Ile Pro Cys Asn Glu Ser Cys Ser Val Val Gly
        210                 215                 220

Lys Val Ile Ala Ser Gln Trp Pro Glu Glu Thr Phe Gly
225                 230                 235

<210> SEQ ID NO 9
<211> LENGTH: 360
<212> TYPE: PRT
<213> ORGANISM: pCSJ Fragment

<400> SEQUENCE: 9

Val Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                    85                  90                  95

Ser Met Val Glu Arg Ser Gly Val Glu Ala Cys Lys Ala Ala Val His
                    100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                    165                 170                 175
```

-continued

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Ser Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
            355                 360

<210> SEQ ID NO 10
<211> LENGTH: 91
<212> TYPE: PRT
<213> ORGANISM: pCSJ Fragment

<400> SEQUENCE: 10

Met Val Arg Trp Thr Leu Trp Asp Thr Leu Ala Phe Leu Leu Leu Leu
  1               5                  10                  15

Ser Leu Leu Leu Pro Ser Leu Leu Ile Met Phe Ile Pro Ser Thr Phe
                 20                  25                  30

Lys Arg Pro Val Ser Ser Trp Lys Ala Leu Asn Leu Arg Lys Thr Leu
             35                  40                  45

Leu Met Ala Ser Ser Val Arg Leu Lys Pro Leu Asn Cys Ser Arg Leu
         50                  55                  60

Pro Cys Val Tyr Ala Gln Glu Thr Leu Thr Phe Leu Leu Thr Gln Lys
 65                  70                  75                  80

Lys Thr Cys Val Lys Asn Tyr Val Gln Lys Glu
                 85                  90

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
gtaaaatagt caacacgcgc ggtgttagat atttatc                           37

THERMOSTABLE PHAGE LAMBDA OPERATOR MUTANTS FOR REGULATING GENE EXPRESSION

DESCRIPTION

The present invention concerns a method for selecting new $P_R$ or $P_L$ operator sequences from lambdoid phages which have a different thermostability compared to the wild-type sequence with regard to binding a repressor. In addition new mutated $P_R$ or $P_L$ operator sequences and their application for the temperature-regulated expression of genes and for the production of improved vaccines are disclosed.

The initiation of transcription of the $O_R$-$O_L$ region of the bacteriophage lambda and other lambdoid phages is negatively and positively regulated by a repressor which is the product of the cI gene (see review article Ptashne et al., Cell 19 (1980), 1–11). In the $O_R$ region three operator sequences ($O_R1$, $O_R2$ and $O_R3$) overlap the promoters $P_R$ and $P_{RM}$ which are orientated in different directions. $P_R$ controls the transcription of genes which are responsible for the lytic multiplication cycle of the phage whereas $P_{RM}$ is the promoter for the lambda cI gene which is responsible for maintaining the lysogenic state. The lambda repressor cI binds co-operatively to the operator sequences $O_R1$ and $O_R2$ with the result that $P_R$ is repressed and $P_{RM}$ is activated.

In addition the bacteriophage lambda also contains a further operator region $O_L$ which also contains three operator sequences ($O_L1$, $O_L2$ and $O_L3$). The expression of the lambda N gene can be repressed by the $P_L$ promoter by binding of the cI repressor to this $O_L$ operator region.

Promoters of the bacteriophage lambda in particular the $P_L$ and the $P_R$ promoter have been used for a long time in recombinant DNA technology for heterologous temperature-regulated gene expression in E. coli (cf. Hedgpeth et al., Molec. Gen. Genet. 183 (1978), 197–203 and Bernard et al., Gene 5 (1979), 59–76; Buell et al., Nucleic Acids Res. 13 (1985), 1923 and Shatzman and Rosenberg, Methods Enzymol. 152 (1987), 661). A temperature-sensitive lambda repressor cI857 is used in these expression systems which represses the $P_L$ and $P_R$ transcription at low temperatures up to 30° C. but allows a gene expression at higher temperatures.

An advantage of this lambda expression system is that the gene expression can be induced in a simple manner by increasing the temperature and no addition of chemical inducers is necessary for this. However, a serious disadvantage is that the repression of gene expression only occurs up to relatively low temperatures of not more than 30° C., which is a temperature at which only a slow bacterial growth occurs. Hence the object of the invention was to provide an improved system for lambda $P_L$ or $P_R$ gene expression which enables a repression at variable higher temperatures.

This object is achieved by providing mutated $P_R$ or $P_L$ operator sequences from lambdoid phages which, compared to the wild-type operator sequence, have a different and in particular higher thermostability with regard to the binding of a temperature-sensitive repressor. The finding that lambda expression systems with an improved thermostability can be produced at all is extremely surprising since, apart from the temperature-sensitive lambda cI857 mutant, no other temperature-sensitive cI mutants are known but only those mutations in the cI repressor are known which make the molecule more resistant to thermal inactivation (Hecht et al., Proteins 1 (1986), 43–46 and Das and Mandal, Mol. Gen.Genet. 204 (1986), 540–542). It was even more surprising that mutations which lead to an improved thermostability are located in the operator DNA sequence and not in the DNA sequence coding for the repressor molecule. Thus for example a mutation of the lambda $O_R2$ operator sequence is known from the literature which leads to a complete loss of repressor binding (Hawley et al., J.Biol.Chem. 260 (1985), 8618–8626).

A method is provided for identifying suitable mutants which enables the selection of mutated $O_R$ or $O_L$ operator DNA sequences from lambdoid phages which have a different thermostability compared to the wild-type sequence with regard to binding a repressor in which the method is characterized in that (a) a DNA cassette is prepared which contains a selection gene under the operative control of an expression control sequence comprising at least one $O_R$ or $O_L$ operator sequence from a lambdoid phage and a promoter, (b) the operator DNA sequence is subjected to a mutagenesis and (c) the mutated operator DNA sequences are analysed.

The lambdoid phages are preferably selected from the group comprising the phage lambda, phage 21, phage 22, phage 82, phage 424, phage 434, phage D326, phage DLP12, phage gamma, phage HK022, phage P4, phage Phi80, phage Phi81, coliphage 186 and recombinant variants thereof. The said phages are very similar with regard to the mechanism of repression of gene expression by means of a cI repressor (Johnson et al., Nature 294 (1982), 217–223). Recombinant variants of the said phages e.g. lambda imm434 can be obtained by substitution of individual genome fragments within the said phages (cf. for this Hendricks et al., Lambda 2 (1983), R. W. Hendricks, J. W. Roberts, F. W. Stahl and R. A. Weissberg (publisher), Cold Spring Harbor Laboratory Press, New York). The phage lambda or a recombinant variant thereof is preferably used as the lambdoid phage e.g. lambda imm434. An operator DNA sequence from the operator regions $O_R$ (SEQ ID NO.1) or/and $O_L$ (SEQ ID NO.3) of the phage lambda and in particular one of the operator sequences $O_R1$, $O_R2$ and $OR^3$ or $O_1$, $O_L2$ and $O_L3$ contained therein is particularly preferably used for the mutagenesis. The operator sequence $O_R2$ is most preferred.

The selection gene for the DNA cassette which is brought under the operative control of the expression control sequence containing the mutated operator sequence, preferably a lambda operator/promoter region, is preferably a suicide gene which when expressed leads to the death of the bacterial cell and thus serves as a selection marker for identifying suitable mutants. The suicide gene should be so strongly repressed at a temperature at which the lambda repressor binds to the mutated operator sequence that a bacterial cell containing the DNA cassette can grow. When the maximum temperature at which the repressor can still bind to the operator is exceeded, the suicide gene is expressed and the bacterial cell is destroyed. This enables a simple and direct selection of suitable mutated operator sequences. A suitable suicide gene is the E lysis gene from the phage PhiX174 as well as homologues and derivatives derived therefrom (Hutchison and Sinsheimer, J.Mol.Biol. 18 (1966), 429–447; Witte et al., Multifunctional safety vector systems for DNA cloning, controlled expression of fusion genes and simplified preparation of vector DNA and recombinant gene products, in BioTech Forum, Advances in Molecular Genetics 3, pp 219–239, publisher: Issinger, O. -G., Henke, J., Kämpf, J., Driesel, A. J., Huthing Verlag 1991, Heidelberg). Further examples of suitable lysis genes are GEF (Poulsen et al., Mol.Microbiol. 5 (1991), 1627–1637) and Kil (Reisinger et al., Virology 193 (1993), 1033–1036). On the other hand the selection gene can also be a reporter gene such as e.g. the β-Gal gene.

In order to produce mutants the operator DNA sequence is preferably subjected to-a site-specific mutagenesis using one or several oligonucleotides for example according to the method of Kunkel (Proc.Natl.Acad.Sci. USA 82 (1985), 488–492) or they are obtained by selection in a mutator bacterial strain e.g. an E. coli mutD or mutL mutator strain such as E. coli ES1578 (Wu et al., Gene 87 (1990), 1–5). The mutated operator DNA sequences are preferably selected by determining the ability to bind to a temperature-sensitive cI repressor in particular to the temperature-sensitive cI857 repressor. For this the DNA cassette which is preferably located on a vector is transformed into a bacterial cell which contains a gene coding for a temperature-sensitive cI repressor. This gene may also be present on a vector (Remaut et al., Gene 15 (1981), 81–93). On the other hand it is possible to use a bacterial cell which contains such a repressor gene in its chromosome e.g. E. coli M5219 (cf. e.g. Shimatake and Rosenberg, Nature 292 (1981), 128).

Mutants which are resistant to lysis at different temperatures can be identified in a simple manner by culturing the bacterial cells transformed with a lysis cassette which contain the mutated operator DNA sequences. Up to now it has been possible to identify several mutants which are resistant to a lysis at temperatures up to 33° C., 35° C., 37° C. and 39° C. These bacteria contain mutated operator DNA sequences which allow binding of the repressor up to the respective temperature. A particularly preferred example is a mutant to which the cI857 repressor binds up to a temperature of about 37° C. Compared to the wild-type the mutation is a single base substitution in the $O_R2$ section of the lambda $O_R$ operator region. The sequence of this mutated lambda $O_R$ operator is shown in SEQ ID NO.2.

An additional subject matter of the invention are mutated $O_R$ or $O_L$ operator sequences from lambdoid phages which have a different thermostability compared to the wild-type sequence with regard to binding of a repressor and which are obtainable by the selection methods described above. The mutated $O_R$ or $O_L$ operator sequences preferably have an increased thermostability with regard to the binding of a temperature-sensitive repressor and in particular of the temperature-sensitive cI repressor. The mutated operator sequences particularly preferably have a thermostability that is increased by about 3 to 10° C., in particular by about 7 to 9° C. compared to the wild-type sequence.

Since the selection method according to the invention is preferably carried out on $O_R$ or $O_L$ operator sequences which are derived from the phage lambda, the present invention in particular concerns mutated lambda $O_R$ or $O_L$ operator sequences which are variants of the $O_R$ operator sequences shown in SEQ ID NO.1 or variants of the $O_L$ operator sequences shown in SEQ ID NO.3. Variant in this connection is understood as an operator sequence which differs from the wild-type sequence in at least one sequence position by insertion, deletion or substitution of bases. The differences are particularly preferably in the region of the sections $O_R1$, $O_R2$ or $O_R3$ and $O_L1$, $O_L2$ and $O_L3$. A specific example of a mutated lambda operator sequence according to the invention is the lambda $O_R$ operator sequence shown in SEQ ID NO.2.

The mutated operator sequences allow the production of new temperature-regulated systems for gene expression in which microorganisms and in particular bacteria can be cultured in a repressed state at variable temperatures and preferably at higher temperatures than have been previously possible in particular at 33 to 39° C. Hence a subject matter of the invention is the use of the mutated $O_R$ or $O_L$ operator sequences for the temperature-regulated expression of genes in bacteria and in particular in gram-negative bacteria such as E. coli. Combination of a wild-type $O_R$ or $O_L$ operator region and at least one operator region which contains a mutated operator sequence according to the invention or combination of several operator regions which contain mutated operator sequences according to the invention with different thermostabilities even enables a temperature-regulated sequential expression of genes.

Vectors and bacterial strains in which the inventive mutated operator sequences can be used for the temperature-regulated expression of genes are familiar to a person skilled in the art. In this case the expression systems known from the prior art containing the lambda cI857 repressor in combination with a suitable promoter e.g. the lambda $P_L$ or lambda $P_R$ promoter can be used (cf. e.g. Sambrook et al., Molecular Cloning, A Laboratory Manual, 2nd Edition, 1989, Cold Spring Harbor Laboratory Press, New York, A further subject matter of the present invention is a nucleic acid comprising a bacterial expression control sequence i.e. a sequence containing a promoter and operator regions which contains a mutated $O_R$ or $O_L$ operator sequence according to the invention in operative linkage with a protein-coding sequence. The protein-coding sequence can for example be a sequence coding for a eukaryotic protein or polypeptide or a bacterial gene e.g. the E-lysis gene.

An additional subject matter of the present invention is a vector which contains at least one copy of the bacterial expression control sequence in operative linkage with the protein-coding sequence. This vector can be any prokaryotic vector e.g. a chromosomal vector such as a bacteriophage or an extrachromosomal vector such as a plasmid. Suitable prokaryotic vectors are described for example by Sambrook et al., Supra, chapters 1–4.

Yet a further subject matter of the present invention is a bacterial cell which is transformed with a nucleic acid according to the invention or with a vector according to the invention. In a preferred embodiment the cell is a gram-negative prokaryotic cell, particularly preferably an E. coli cell. The cell preferably contains the nucleic acid or the vector integrated into its chromosome and in addition contains a gene for a cI repressor from a lambdoid phage in particular the gene for the lambda cI857 repressor.

A particularly preferred application of the mutated operators according to the invention is in the field of vaccine production. So-called "bacterial ghosts" are known as vaccines from the prior art i.e. bacterial coats that can be prepared from gram-negative bacteria such as E. coli, Salmonella typhimurium, Klebsiella pneumoniae, Actinobacillus pleuropneumoniae etc. by means of protein-E-induced lysis. These ghosts whose cell surface properties and repertoire of surface antigens that can be recognized by the immune system are very similar to the active pathogen, produce a protective cellular or/and humoral immune response in various animal models.

The process for preparing the ghosts is based on the stringent controlled expression of the E-lysis gene from PhiX74, whose expression product forms a tunnel through the bacterial cell wall coat and thus leads to a pouring out of the cell contents of the host cell. This lethal gene for the cells can be regulated by means of a lambda repressor e.g. the temperature-sensitive lambda repressor cI857 which, as described above, loses its function at temperatures above 30° C. As a result, the bacterial cultures that have previously been used to produce bacterial ghosts have had to be cultured at low temperatures, preferably at 28° C.

Although this method leads to satisfactory results with regard to the immunogenicity of the ghosts that are produced, an improvement of the bacterial culture is urgently required since the repertoire of antigenic determinants on the bacterial surface can change depending on the external conditions. Since pathogenic bacteria which infect humans or animals usually colonize at an environmental temperature of 37 to 39° C., this natural environmental temperature should also be maintained during the production process for the ghosts.

A process for producing bacterial ghosts which achieves this object is provided by using the mutated operator sequences according to the invention. These operator sequences allow growth of the bacteria up to a temperature range of preferably 35 to 39° C. and allow lysis when the temperature is increased from 37 to 42° C. This changed lysis behaviour enables the pathogens to be cultured near to the body temperature of the vaccine candidate which is extremely important for the composition of the external membrane. Furthermore the new lysis cassette can also be used as a safety cassette in live vaccines since for example in humans the inoculated bacteria are killed when fever is induced (39° C.).

Hence a subject matter of the invention is a vaccine composition which contains a live bacterial cell according to the invention as the active ingredient optionally together with pharmaceutically tolerated auxiliary substances, additives and carrier substances. The live bacterial cell contains a nucleic acid comprising a bacterial expression control sequence with a mutated operator sequence in operative linkage preferably with a lysis gene. Yet a further subject matter of the present invention is a vaccine composition which contains a bacterial ghost as an active ingredient optionally together with pharmaceutically tolerated auxiliary-substances, additives and carrier substances wherein the bacterial ghost is obtainable by culturing a bacterial cell according to the invention at temperatures of 35–39° C. and subsequently lysing the bacterial cell by increasing the temperature. Bacterial cells suitable as vaccines are in particular gram-negative bacteria such as *E. coli* for example the strains STEC, EHEC, 078:K80, Salmonellae such as *S.choleraesuis, S.enteritidis* and *S.typhimurium, Pasteurella multocida, Pasteurella haemolytica, Bordetella bronchiseptica, Klebsiella pneumoniae, Actinobacillus pleurbpneumoniae, Haemophilus influenzae, Vibrio cholerae, Helicobacter pylori, Alcaligenes eutrophus, Campylobacter jejuni* and *Pseudomonas aeruginosa*.

The vaccine compositions modified according to the invention can be transferred orally, aerogenically or parenterally to the vaccine candidates. The route which the corresponding microorganisms naturally select for the infection and for the initial stages of establishing an infectious disease are preferably selected for the application of the vaccine. Since all surface properties are retained in the vaccines according to the invention, this application can result in a local induction of the immune response as also occurs in the natural infection process.

As described above the use of mutated operator sequences according to the invention enables the development of vaccines that can be lysed in a controlled manner when a target temperature is exceeded. Furthermore it is, however, also possible to provide a cold-sensitive suicide cassette which on release into the environment kills gram-negative bacteria that are used as a live vaccine. Hence combination of two genetic regulation systems enables the bacteria to die as a result of the expression of a suicide gene when a target value for the environmental temperature is exceeded. This safety cassette ensures that the live vaccines are killed even if they are eliminated from the organisms.

Hence the invention concerns a nucleic acid comprising (a) a first bacterial expression control sequence which contains an $O_R$ or $O_L$ operator sequence from a lambdoid phage and to which a first temperature-sensitive cI repressor from lambdoid phages can bind in operative linkage with a sequence coding for a second repressor wherein the second repressor cannot bind to the first bacterial expression sequence and (b) a second bacterial expression control sequence to which the second repressor can bind which is in operative linkage with a suicide gene.

The components (a) and (b) can be covalently linked, together e.g. be present on a single vector or be separate from one another e.g. present on different vectors or be located separately or together on the chromosome of a recipient bacterium.

Yet a further subject matter of the present invention is a bacterial cell which contains at least one copy of a nucleic acid as described above. In addition the bacterial cell advantageously contains a gene for the first repressor. The first repressor is preferably the temperature-sensitive cI857 repressor.

The safety cassette according to the invention preferably contains a gene which codes for a temperature-sensitive cI repressor e.g. the repressor cI857 and a gene which codes for a second repressor wherein this gene is under the control of a lambda promoter/operator region to which the temperature-sensitive repressor binds. The second repressor in turn controls the expression of another gene e.g. a suicide gene such as the E-lysis gene. The temperature-sensitive lambda repressor is inactive at 37° C. so that the second repressor is expressed which in turn represses the expression of the suicide gene.

When the temperature is reduced the temperature-sensitive lambda repressor binds to the operator so that the expression of the second repressor is blocked which leads to an expression of the suicide gene. A first expression control sequence is preferred for this safety cassette which contains the mutated lambda operator since this enables an improved and more rapid activation of the suicide gene.

The second repressor can be any repressor e.g. a lac repressor. However, it is preferable to use an additional repressor from lambdoid phages e.g. cI from the phage 434 which is not temperature-sensitive and binds to its own operator sequence but does not bind to the sequence recognized by the lambda repressor cI857.

It is particularly preferable for the development of live vaccines to incorporate a heat as well as a cold regulation element. This incorporation is preferably achieved by homologous recombination into the chromosome of the vaccine bacterium.

Thus the present invention also concerns a bacterial cell which, in addition to the two components (a) and (b), contains a third bacterial expression control sequence as component (c) which contains a mutated operator sequence according to the invention in operative linkage with a suicide gene.

These bacterial cells can also be used in vaccine compositions and especially for live vaccines. In this manner it is possible to produce heat or/and cold-sensitive safe live vaccines which lead to death of the vaccine bacteria when the body temperature of the vaccine candidate is increased e.g. by fever or/and when they are excreted into the environment.

BRIEF DESCRIPTION OF THE DRAWINGS

It is intended to additionally elucidate the invention by the following figures, sequence protocols and examples.

Figure 1A:
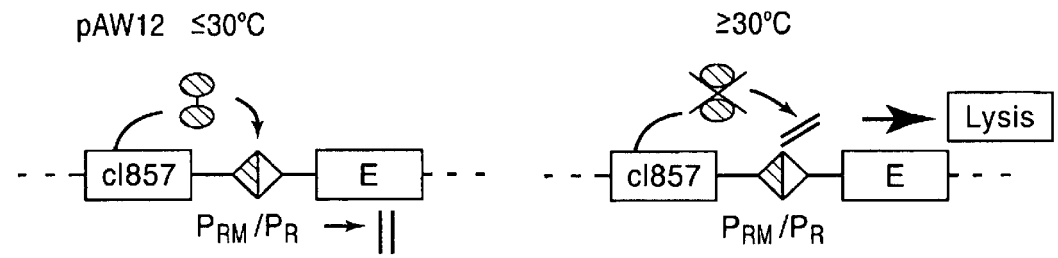
FIG. 1a shows a schematic representation of a lysis cassette of the prior art comprising a lambda $O_R$ wild-type region, the lambda cI857 gene under the control of the promoter $P_{RM}$ and the E lysis gene under the control of the promoter $P_R$.

SEQ-ID NO.1 shows the nucleotide sequence of the lambda $O_R$ operator; the operator sequence $O_R 3$ extends from position 11–27; the operator sequence $O_R 2$ extends from position 34–41;

the operator sequence $O_R 1$ extends from position 58–74;

SEQ ID NO.2 shows the nucleotide sequence of a mutated lambda $O_R$ operator which, compared to the wild-type sequence, has a substitution of T→C at position 42;

SEQ ID NO.3 shows the nucleotide sequence of the lambda $O_L$ operator; the operator sequence $O_L 3$ extends from position 11–27; the operator sequence $O_L 2$ extends from position 31–47;

the operator sequence $O_L 1$ extends from position 55–70;

SEQ ID NO. 4 to 6 show a 1601 bp long DNA fragment of the plasmid pAW12; bp 1–983 are derived from the bacteriophage lambda (position 37125–38107; cf. Sanger et al., J.Mol.Biol. 162 (1982), 729–773) and contain the lambda cI857 gene (position 816-106; SEQ ID NO.5) as well as the mutated $O_R$ operator region (mutation at position 858 T→C); bp 1023–1601 are derived from the phage PhiX174 (position 447–1026; cf. Sanger. et al., J.Mol.Biol. 125 (1978), 225–246) and contain the E-lysis gene (position 1144-1416; SEQ ID NO.6);

SEQ ID NO. 7 to 10 shows a 2834 bp long DNA fragment of the plasmid pCSJ; bp 1–983 are derived from the bacteriophage lambda (position 37125–38107) and contain the cI857 gene (position 816–106; SEQ ID NO.5) as well as the mutated lambda $O_R$ region (mutation at position 858 T→C; bp 990–2230 are derived from the E. coli lac operon subcloned on the plasmid pMC7 (Calos, Nature 274 (1978), 762–765) and contain the lacI repressor gene (bp 1025–2104; SEQ ID NO.9) and the lac promoter/operator; bp 2256–2834 are derived from the bacteriophage PhiX174 (position 447-1026) and contain the E-lysis gene (bp 2377–2649; SEQ ID NO.10).

EXAMPLES

Example 1

1.1 Random Mutagenesis of the Lambda $O_R$ Operator Region

The plasmid pAW12 (Witte and Lubitz, Eur.J.Biochem. 180 (1989), 393–398) was selected as the starting material which contains the lysis gene E from the bacteriophage PhiX174 under the control of the lambda $P_R$ promoter as well as the associated repressor gene cI857. The aim of this experiment was to change the lysis cassette so that the lysis gene E is not already activated at 30° C. but at higher temperatures. For this the E. coli mutator strain ES1578 (Wu et al., (1990), supra) was transformed with the lysis plasmid and a selection was carried out for clones with a changed temperature profile of cell lysis.

For this the mutated clones produced by the transformation were detected after being stamped onto test plates containing lysis selective medium (LB containing 1% SDS) and incubated at different temperatures (e.g. 33° C., 34° C., 35° C., 36° C., 37OC, 38° C., 39° C., 40° C., 41° C.). The changed lysis profile of the lysis cassette in liquid culture was exactly determined by plasmid extraction and subsequent transformation into a non-mutator test strain.

The type of mutation was determined by subcloning the mutagenized lysis cassettes into a sequencing plasmid. In addition the lysis gene E was substituted by the β-galactosidase gene for a functional check. It was then possible on the basis of a simple β-gal test to quantitatively measure the repressed or active state of the gene cassette.

In this manner is was possible to obtain several clones with a different temperature lysis profile. These clones allowed growth of the bacteria in a temperature range of 33–39° C. and did not lead to lysis of the bacteria until the temperature was further increased to 37–42° C.

A mutation of the $O_R$ operator region (SEQ ID NO.2) was identified by sequencing a mutated clone which had a thermostability up to 37° C.

1.2 Verification of the Mutation

In order to verify the mutation obtained in example 1.1. a site-specific mutagenesis of the lambda $O_R$ wild-type sequence was carried out using an oligonucleotide.

The mutagenesis was carried out according to the protocol of Kunkel (Proc.Natl.Acad.Sci. USA 82 (1985), 488–492).

4 ml overnight culture of the E. coli strain CJ236 (dut⁻, ung⁻) was added to 50 ml LB medium (+10 μg/ml chloramphenicol and 0.25 μg/ml uridine) and shaken for 30 min at 37° C. Then 100 μg/ml M13 phages was added and it was incubated for 6 h at 37° C.

The culture was centrifuged in 2 SS34 centrifuge tubes for 10 min at 14000 rpm and 4° C., the supernatant was decanted into new tubes and again centrifuged for further purification.

The phages were precipitated for 1 h at 4° C. by addition of 5 ml 5×polyethylene glycol/NaCl. They were then centrifuged for 10 min at 14000 rpm and 4° C. and the supernatant was discarded.

The pellet was dried, suspended in 0.8 ml TES buffer (0.1 M Tris HCl, pH 8; 0.3 M NaCl; 1 mM EDTA) and incubated for 1 h at 4° C. The suspension was divided into 2 Eppendorf vessels and centrifuged for 5 min at 5000 rpm. The supernatant in which the disrupted phages were located was removed and subjected to a phenol/chloroform extraction to isolate the DNA. The resulting DNA was precipitated with a 2.5-fold volume of 96% ethanol, washed with 70% ethanol and taken up in 60 μl $H_2O$.

An oligonucleotide with the sequence 5'-GTA AAA TAG TCA ACA CGC GCG GTG TTA GAT ATT TAT C-3' (SEQ ID NO.11) was phosphorylated. For this 20 μl $H_2O$, 20 μl oligonucleotide (20 ng), 4.5 μl kinase buffer (Stratagene) and 0.5 μl polynucleotide kinase (5 U, Stratagene) was incubated for 1 h at 37° C. Then 7 μl 0.1 M EDTA was added and it was heated for 10 min to 65° C.

For the annealing 20 μl phosphorylated oligonucleotide, 3.5 μl single-stranded DNA template (1 μg ssDNA produced as described above) and 1.4 μl 20×SSC buffer were heated for 5 min to 70° C., slowly cooled to 25° C. and then placed on ice.

For the extension 10 μl of the reaction mixture from the annealing mixture, 37.5 μl XL buffer (27 mM Hepes pH 7.8, 5 mM of each dNTP, 13 mM $MgCl_2$, 2.7 mM dithiothreitol, 1.3 mM ATP, 1 μl ligase (1 U, Boehringer Mannheim), 1.5 μl T4 polymerase (1.5 U, Boehringer Mannheim), 1.5 μl T4 gene32 protein (8 μg, Boehringer Mannheim) were incubated for 10 min on ice, 10 min at room temperature and 2 h at 37° C. After 1 h 1 μl ligase and 1 μl T4 DNA polymerase was added. After completion of the incubation the reaction was stopped by adding 3 μl 0.25 M EDTA.

For the transformation 100 μl competent *E. coli* cells JM103 (Messing et al., Nucleic Acids Res.9 (1981), 309–321) was admixed with 10 μl DNA from the extension mixture and incubated for 1 h or more on ice. After a heat shock for 2.5 min at 42° C., 0.2 ml fresh JM103 cells was added in the logarithmic growth phase. The cells were mixed with 3 ml soft agar and inoculated on an LB agar plate. They were subsequently incubated overnight at 37° C.

In order to identify the mutants, plaques were pricked out with a Pasteur pipette and used to inoculate 5 ml LB medium to which 400 μl of an overnight culture of *E. coli* JM103 had been added. After 3 h growth at 37° C., the cells were centrifuged. Double-stranded M13 plasmids were obtained from the cell pellet by means of plasmid preparation. Single-stranded M13 phages could be isolated from the supernatant.

Example 2

Analysis of the mutagenized lysis cassettes FIGS. 1 and 2 shows different E-specific lysis cassettes with different temperature inductions of the lysis function.

Figure 1B:
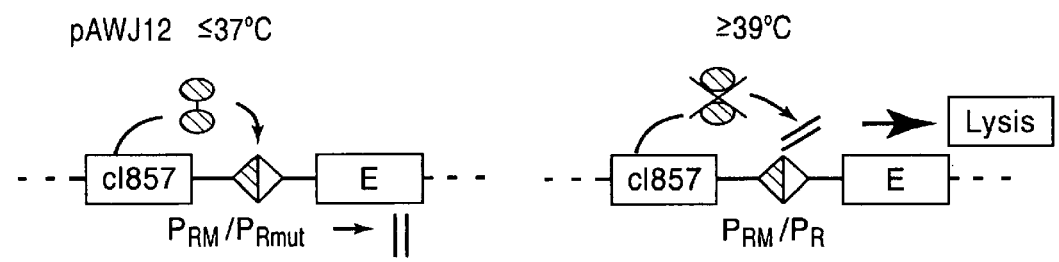
FIG. 1b shows a schematic representation of a lysis cassette according to the invention which contains a mutated lambda $O_R$ sequence.

In FIG. 1*a* which contains the wild-type lambda $O_R$ operator sequence, the function of the E-lysis gene is repressed up to 30° C. by the cI857-coded repressor protein on the preceding lambda $P_R$ promoter/operator region. cI857-specific repressor molecules are thermally inactivated at temperatures above 30° C. and the expression of the E gene is induced. FIG. 1*b* shows the plasmid pAWJ12 which contains a mutated operator sequence (SEQ ID No.2) so that the repression of the lysis function of the gene E by cI857 occurs up to 37° C. and the lysis function is not induced until 39° C. or higher temperatures are reached.

Figure 2A:
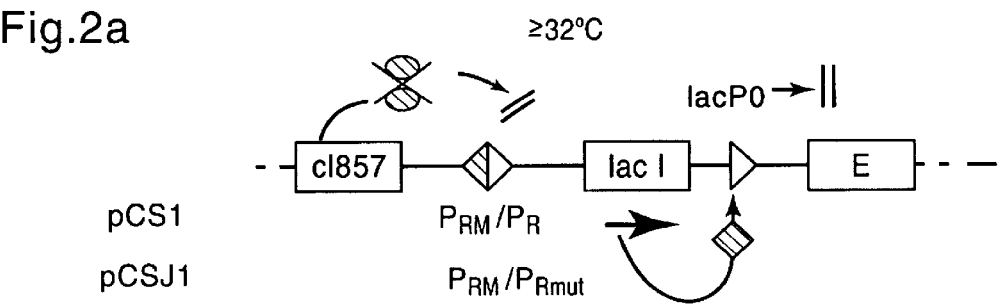
FIG. 2a shows a schematic representation of a cold-sensitive safety cassette comprising a wild-type (pCS1) or mutated (pCSJ1) $O_R$ operator sequence, the lambda-cI857 gene under the control of the promoter $P_{RM}$, the gene of the lacI repressor under the control of $P_R$ and the E-lysis gene under the control of the lac promoter/operator system at a temperature at which the temperature-sensitive lambda repressor cI857 does not bind to the lambda $O_R$ sequence.
Figure 2B:
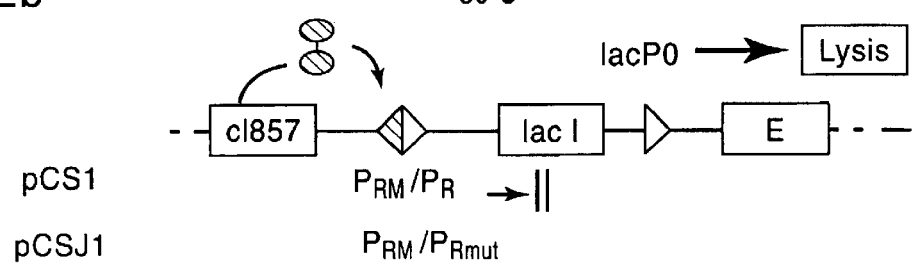
FIG. 2b shows a schematic representation of the safety cassette according to FIG. 2a at a temperature at which the lambda repressor cI857 binds to the lambda $O_R$ operator.

The function of a cold-sensitive safety cassette is elucidated in FIG. 2. FIG. 2*a* shows that the formation of lacI-specific repressor molecules which in turn repress the expression of the E gene is induced in the plasmids pCS1 (wild-type operator) and pCSJ1 (mutated operator) at a temperature of >32° C. (pCS1) or >39° C. (pCSJ1). At a temperature below 30° C. (pCS1) or 37° C. (pCSJ1) functional cI857 repressor molecules are formed which suppress the formation of lacI-specific repressor molecules and thus allow the expression of the E gene (FIG. 2*b*). In the plasmid pCSJ1 the concomitant cell lysis occurs more rapidly than in pCS1.

Figure 3:
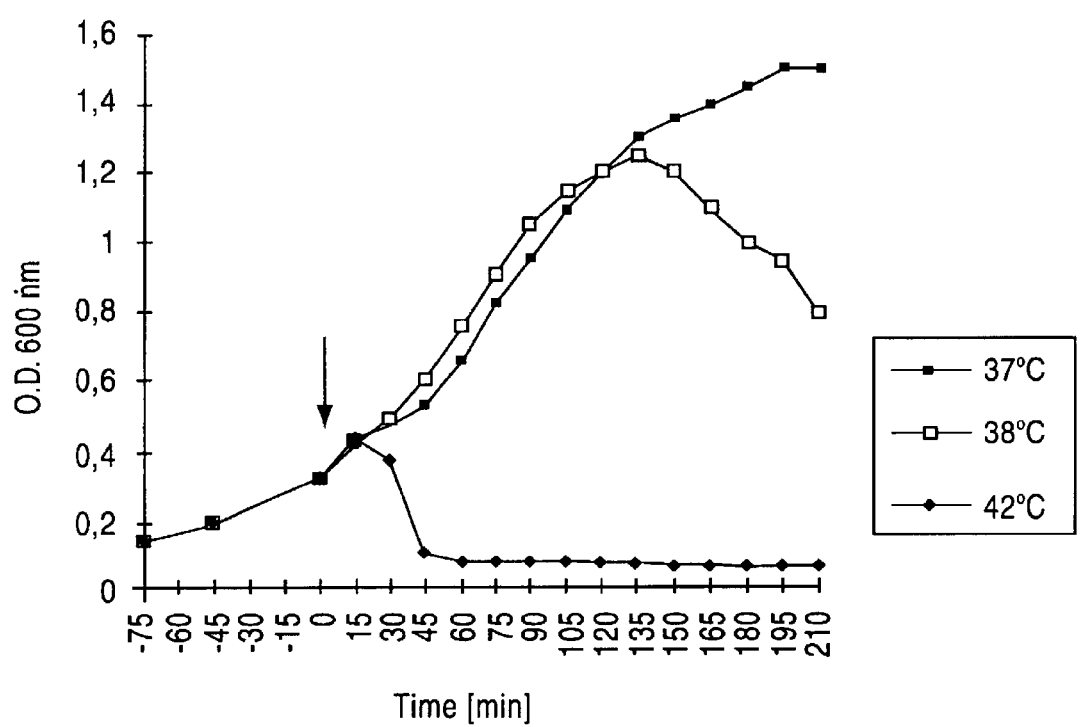
FIG. 3 shows the lysis curve of bacterial cells (optical density versus time) which contain a plasmid with the lysis cassette shown in FIG. 1b.

FIG. 3 shows the lysis curve of a bacterial cell containing the plasmid pAWJ12 (mutated operator). 3 hours after beginning the culture, the temperature was maintained at 37' C. in an aliquot of the bacterial cells and increased in two other aliquots to 38 and 42° C. At 37° C. there was a further growth of the bacteria whereas a lysis already occurred at 38OC. The lysis is considerably increased at 42° C.

Figure 4:
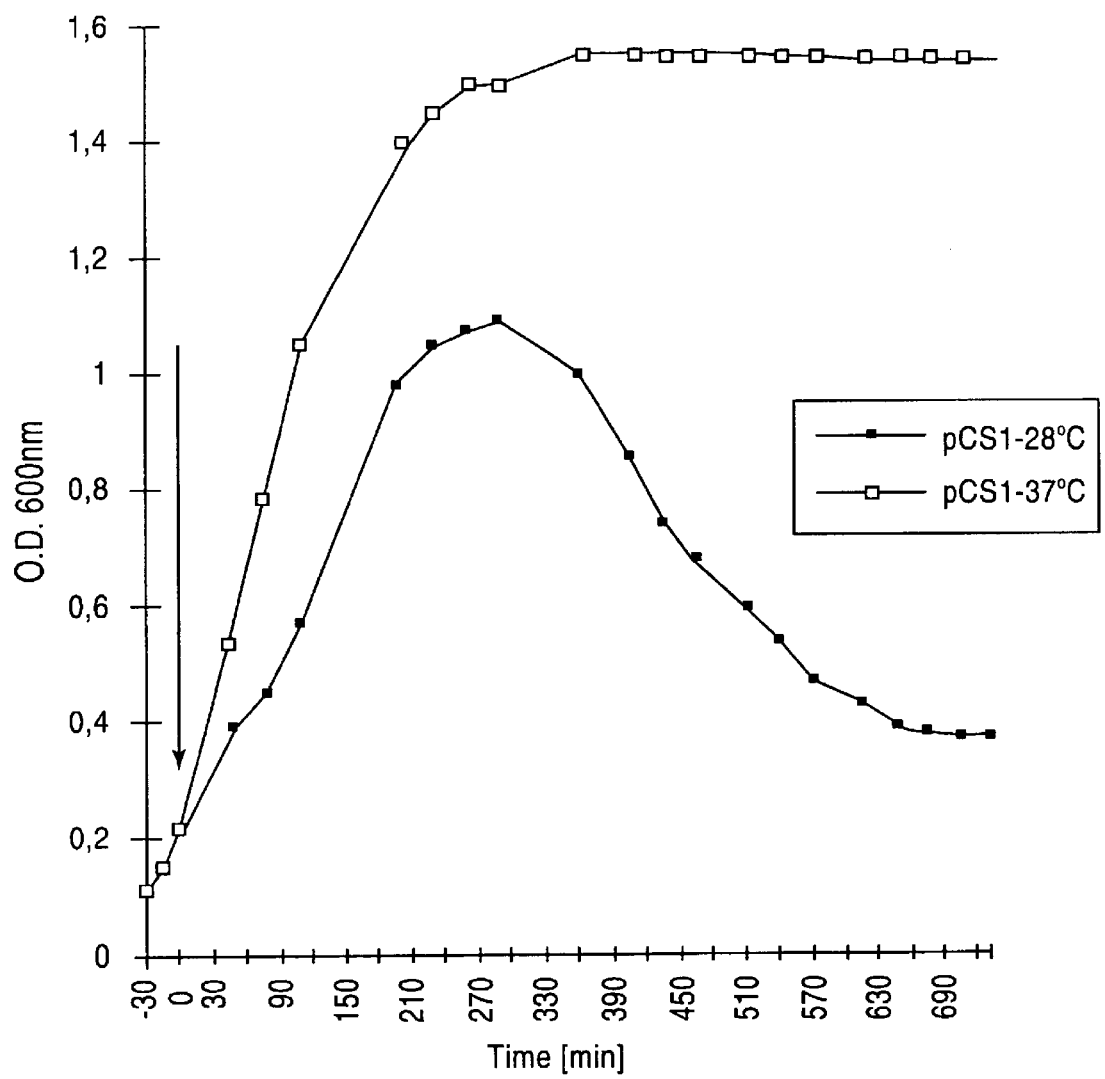
FIG. 4 shows the lysis curve of a bacterial cell which contains a cold-sensitive safety cassette with the wild-type $O_R$ operator and FIG. 5 shows a comparison of lysis curves of bacterial cells which contain a cold-sensitive safety lysis cassette with the wild-type $O_R$ operator (pSC1) or the mutated operator (pCSJ1)
Figure 5:
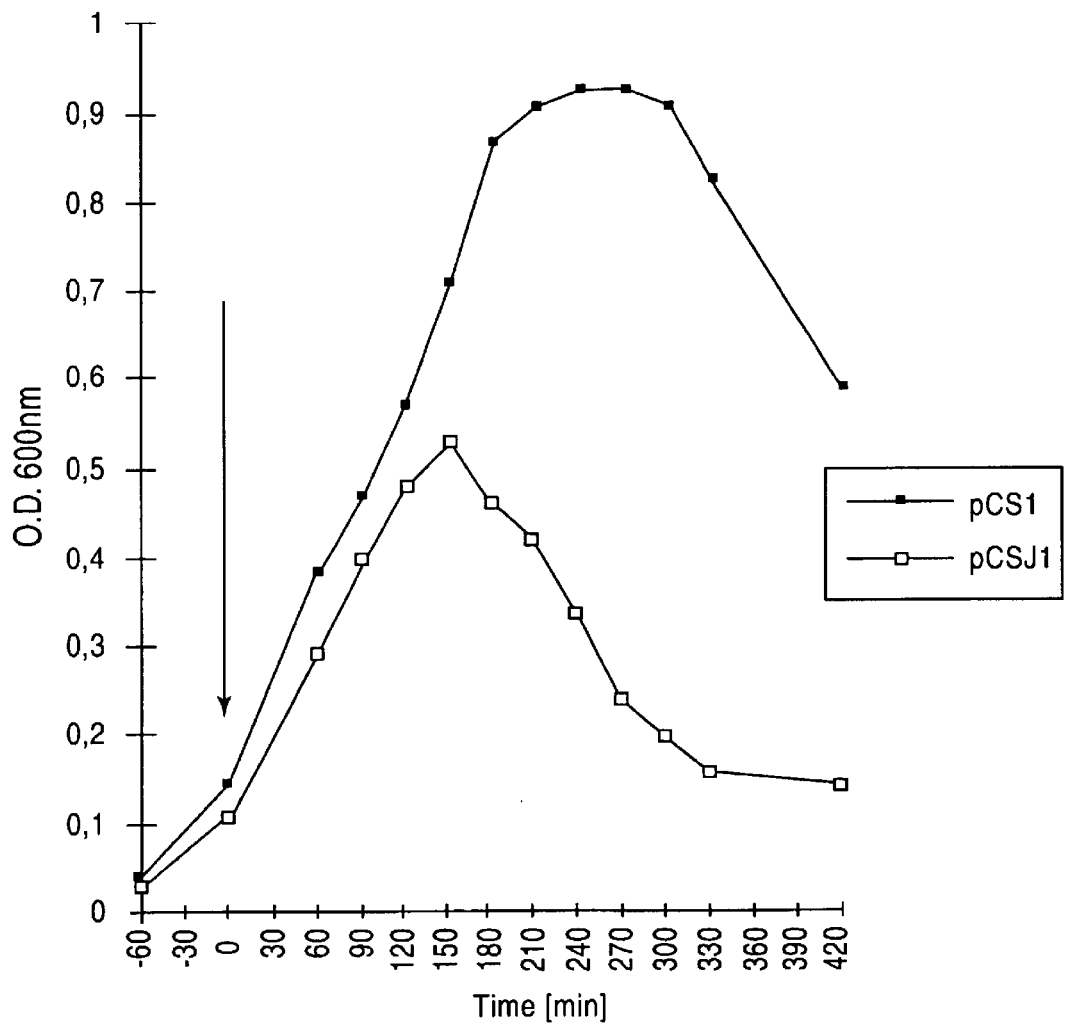

FIGS. 4 and 5 show the function of a cold-sensitive safety cassette. In FIG. 4 bacterial cells which contained the plasmid pCS1 (wild-type operator) were subjected to a temperature change from 37 to 28° C. This reduction in temperature led to the E-lysis gene being switched off and cell death (decrease of the optical density).

FIG. 5 shows a comparison of the lysis rate of bacteria which contain the plasmid pCS1 (wild-type operator) and the plasmid pCSJ1 (mutated operator). It can be seen that the lysis occurs much more rapidly in the bacteria which contain the mutated operator.

Figure 6A:
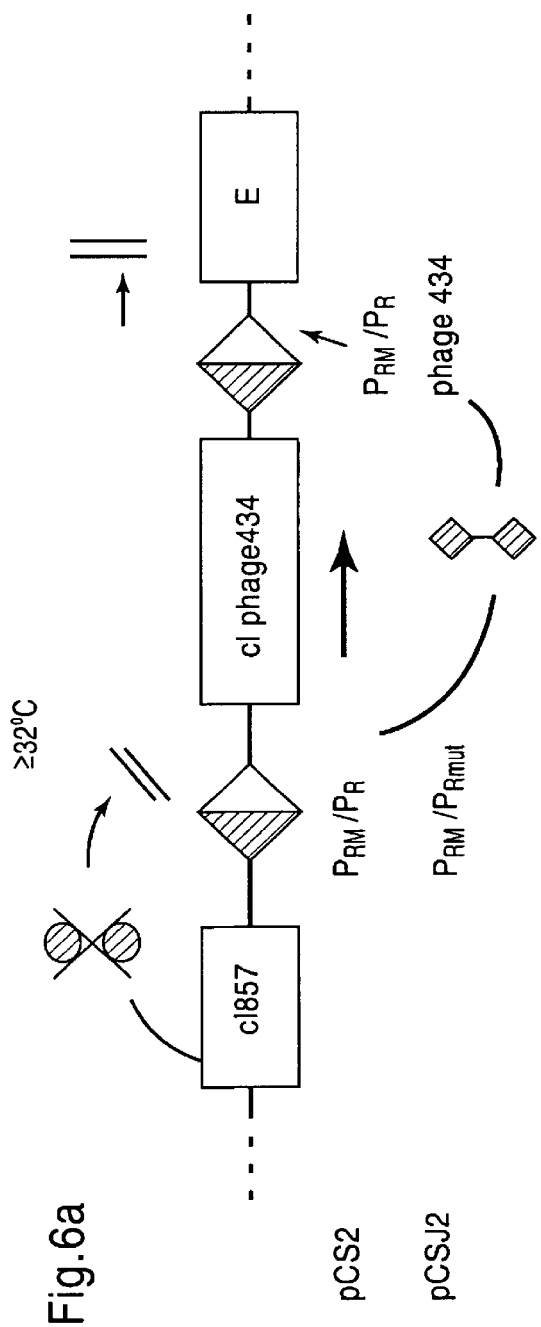
FIG. 6a shows a schematic representation of a cold-sensitive safety cassette comprising a wild-type (pCS2) or mutated (pCSJ2) $O_R$ operator sequence, the lambda cI857 gene under the control of the promoter $P_{RM}$, the gene of the phage 434 cI repressor under the control of lambda $P_R$ and the E lysis gene under the control of the 434 $O_R$ ($P_{RM}$-$P_R$) promoter/operator system at a temperature at which the temperature-sensitive lambda repressor cI857 does not bind to the lambda $O_R$ sequence.
Figure 6B:
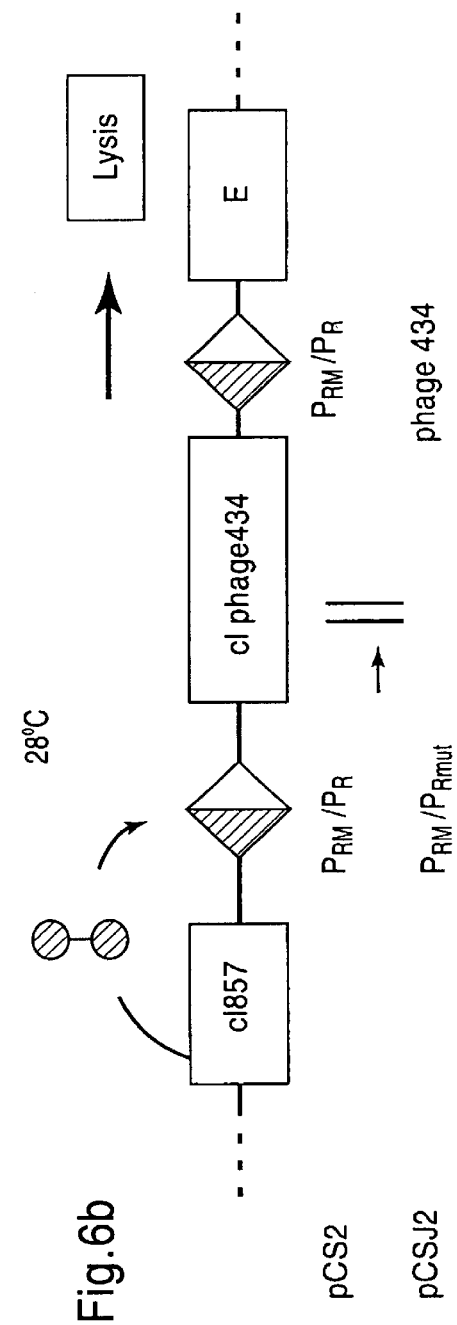
FIG. 6b shows a schematic representation of the safety cassette according to FIG. 6a at a temperature at which the lambda repressor cI857 binds to the lambda $O_R$ operator.

FIG. 6 shows a further cold-sensitive safety cassette. At temperatures at which the lambda cI857 repressor does not bind to the operator the plasmids pCS2 (wild-type operator) and pCSJ2 (mutated operator) form cI-434 repressor molecules which repress the expression of the E gene (FIG. 6*a*). Formation of cI-434-specific repressor molecules is prevented thus allowing expression of the E gene at a temperature at which the cI857 repressor binds to the lambda operator (FIG. 6*b*).

Example 3

In Vivo Analysis of Cold-Sensitive Lysis Cassettes

The killing of bacteria by lowering the temperature after passage through a mouse intestine and excretion into the faeces was determined.

For this $10^{10}$ *E. coli* bacteria were administered once to Balb/c mice and the excreted number of bacteria in the faeces was determined. The evaluation was carried out on *E. coli*-specific Endo plates (Endo, "Zentralbl. Bakt. I orig." 35 (1904) 109–110) using tetracyclin as a marker for the plasmids used. The incubation was carried out at 28° C.

Results:

In the experimental groups *E. coli* NM522 (pCS2), *E. coli* MC4100 (pCS1) and *E. coli* MC4100 (pCSJ1) there was a reduction in the germ count compared to an *E. coli* NM522 (pAWJ-lac) control of at least 99.9%, 98% and 80% measured 10 h and 20 h after administering the *E. coli* bacteria.

What is claimed is:

1. A method for selecting an OR or OL operator DNA sequences from a lambdoid phages wherein said sequence has a different thermostability compared to a wild-type sequence with regard to binding a repressor, wherein said different thermostability results in repression of expression of a gene which is operatively linked to said OR or OL operator DNA sequence from a lambdoid phage until a temperature is reached that is 3 to 10° C. higher than the temperature at which the wild type sequence is capable of repressing the expression of a gene operatively linked thereto, comprising (a) preparing a DNA cassette which contains a selection gene under the operative control of an expression control sequence comprising at least one OR or OL operator DNA sequence from a lambdoid phage and a promoter, (b) intentionally subjecting the operator DNA sequence to a mutagenesis, and (c) analyzing the operator DNA sequences to determine whether said sequences have a different thermostability as compared to a wild-type sequence with regard to binding a repressor, wherein a mutated operator sequence is selected that represses expression of the gene operatively linked thereto at a temperature that is 3 to 10° C higher than the temperature at which the wild type sequence is capable of repressing the expression of a gene operatively linked thereto.

2. The method according to claim 1, wherein the lambdoid phage are selected from the group consisting of phage lambda, phage 21, phage 22, phage 82, phage 424, phage 434, phage D326, DLP12, phage gamma, phage HKO22, phage P4, phage Phi80, phage Phi81, and coliphage 186.

3. The method according to claim 2, wherein said lambdoid phage is phage lambda.

4. The method according to claim 3, wherein said operator DNA sequence is from the operator regions OR and/or OL of the phage lambda.

5. The method according to claim 1, wherein said selection gene is an E-lysis gene from phage PhiX174.

6. The method according to claim 1, wherein the operator DNA sequence is subjected to a site-specific mutagenesis by oligonucleotides or a selection is carried out in a mutator bacterial strain.

7. The method according to claim 1, wherein the operator DNA sequences are analyzed by determining their ability to bind to a temperature-sensitive cl repressor.

8. The method according to claim 7, wherein the temperature-sensitive lambda cl repressor is cl857.

9. An isolated lambda OR operator sequence comprising the sequence shown in SEQ ID NO: 2.

10. A nucleic acid comprising a bacterial expression control sequence containing a an OR or OL operator sequence in operative linkage with a protein-coding sequence, said operating sequence being an OR or OL operator DNA sequence from bacteriophage lambda which has a different thermostability compared to a corresponding wild-type sequence with regard to binding a repressor, wherein said different thermostability results in repression of expression of a gene which is operatively linked to said OR or OL operator DNA sequence from bacteriophage lambda until a temperature is reached that is 3 to 10° C. higher than the temperature at which the wild type sequence is capable of repressing the expression of a gene operatively linked thereto, and wherein said operator sequence is obtained by a method comprising (a) preparing a DNA cassette which contains a selection gene under the operative control of an expression control sequence comprising at least one OR or OL operator DNA sequence from a lambdoid phage and a promoter, (b) intentionally subjecting the operator DNA sequence to a mutagenesis, and (c) analyzing the operator DNA sequences to determine whether said sequences have a different thermostability as compared to a wild-type sequence with regard to binding a repressor wherein a mutated operator sequence is selected that represses expression of the gene operatively linked thereto at a temperature that is 3 to 10° C. higher than the temperature at which the wild type sequence is capable of repressing the expression of a gene operatively linked thereto.

11. The nucleic acid according to claim 10, wherein the protein-coding sequence is a suicide gene.

12. The nucleic acid according to claim 10, wherein the expression control sequence contains a lambda PL or PR promoter.

13. A vector comprising at least one copy of the nucleic acid of claim 10 that comprises a bacterial expression sequence comprising a mutated OR or mutated OL operator sequence in operative linkage with a protein-coding sequence.

14. The vector according to claim 13, wherein said vector is a bacterial chromosomal vector.

15. The vector according to claim 13, wherein said vector is a bacterial extrachromosomal plasmid.

16. A bacterial cell transformed with the nucleic acid of claim 10 that comprises a bacterial expression sequence comprising a mutated OR or mutated OL operator sequence in operative linkage with a protein-coding sequence.

17. A bacterial cell transformed with a vector according to claim 13.

18. A bacterial cell according to claim 16, wherein said nucleic acid is integrated into said cell's chromosome.

19. A bacterial cell according to claim 17, wherein said vector is integrated into said cell's chromosome.

20. A bacterial cell according to claim 16, further comprising a gene for a cl repressor from lambdoid phages.

21. A bacterial cell according to claim 17, further comprising a gene for a cl repressor from lambdoid phages.

22. A bacterial cell according to claim 20, wherein said gene is the lambda c1857 repressor.

23. A bacterial cell comprising at least one copy of a nucleic acid, wherein said nucleic acid comprises (a) a first bacterial expression control sequence which contains an OR or OL operator DNA sequence from a bacteriophage lambda and to which a first cl repressor from lambdoid phages can bind, in operative linkage with a sequence coding for a second repressor wherein the second repressor cannot bind to the first bacterial expression control sequence and (b) a second bacterial expression control sequence to which the second repressor can bind in operative linkage with a suicide gene, wherein said first bacterial expression control sequence is an OR or OL operator DNA sequence from a bacteriophage lambda wherein said sequence has a different thermostability compared to a corresponding wild-type sequence with regard to binding of a repressor wherein said different thermostability results in repression of expression of a gene which is operatively linked to said OR or OL DNA sequence from a bacteriophage lambda until a temperature is reached that is 3 to 10° C. higher than the temperature at which the wild type sequence is capable of repressing the expression of a gene operatively linked thereto, and wherein said operator sequence is obtained by a method comprising (a) preparing a DNA cassette which contains a selection gene under the operative control of an expression control sequence comprising at least one OR or OL operator DNA sequence from a lambdoid phage and a promoter, (b) intentionally subjecting the operator DNA sequence to a mutagenesis, and (c) analyzing the operator DNA sequences to determine whether said sequences have a different thermostability as compared to a wild-type sequence with regard to binding a repressor, wherein a mutated operator sequence is selected that represses expression of the gene operatively linked thereto at a temperature that is 3 to 10° C. higher than the temperature at which the wild type sequence is capable of repressing the expression of a gene operatively linked thereto.

24. A bacterial cell comprising at least one copy of a nucleic acid, wherein said nucleic acid comprises (a) a first bacterial expression control sequence which contains a first OR or OL operator sequence from a bacteriophage lambda and to which a first cI repressor from lambdoid phages can bind, in operative linkage with a sequence coding for a second repressor wherein the second repressor cannot bind to the first bacterial expression sequence and (b) a second bacterial expression control to which the second repressor can bind in operative linkage with a suicide gene, further comprising (c) a third bacterial expression control sequence which contains a second operator sequence in operative linkage with a suicide gene, wherein said second operator sequence is an OR or OL operator DNA sequence from a bacteriophage lambda and wherein each of said first and second operator sequences has a different thermostability compared to a corresponding wild-type sequence with regard to binding of a repressor, wherein said different thermostability results in repression of expression of a gene which is operatively linked to said OR or OL operator DNA sequence until a temperature is reached that is 3 to 10° C higher than the temperature at which the wild type sequence is capable of repressing the expression of a gene operatively linked thereto, and wherein each of said operator sequences is obtained by a method comprising (a) preparing a DNA cassette which contains a selection gene under the operative control of an expression control sequence comprising at least one OR or OL operator DNA sequence from a lambdoid phage and a promoter, (b) intentionally subjecting the operator DNA sequence to a mutagenesis, and (c) analyzing the operator DNA sequences to determine whether said sequences have a different thermostability as compared to a wild-type sequence with regard to binding a repressor, wherein a mutated operator sequence is selected that represses expression of the gene operatively linked thereto at a temperature that is 3 to 10° C. higher than the temperature at which the wild type sequence is capable of repressing the expression of a gene operatively linked thereto.

25. The bacterial cell of claim 23, wherein said bacterial cell further comprises a gene for the first cI repressor.

26. The bacterial cell of claim 24, wherein said bacterial cell further first cI repressor.

* * * * *